United States Patent [19]
Settles

[11] Patent Number: 6,073,499
[45] Date of Patent: Jun. 13, 2000

[54] CHEMICAL TRACE DETECTION PORTAL BASED ON THE NATURAL AIRFLOW AND HEAT TRANSFER OF THE HUMAN BODY

[75] Inventor: Gary S. Settles, Bellefonte, Pa.

[73] Assignee: Penn State Research Foundation, Pa.

[21] Appl. No.: 09/262,880

[22] Filed: Mar. 8, 1999

Related U.S. Application Data

[60] Provisional application No. 60/077,736, Mar. 12, 1998.

[51] Int. Cl.[7] ....................................................... G01N 1/00
[52] U.S. Cl. ..................................... 73/864.81; 73/864.34
[58] Field of Search ........................... 73/863.31, 863.33, 73/863.11, 863.12, 863.21, 863.23, 864, 864.31, 864.33, 864.34, 864.71, 864.84, 864.81

[56] References Cited

U.S. PATENT DOCUMENTS

| | | |
|---|---|---|
| 4,045,997 | 9/1977 | Showalter et al. . |
| 4,202,200 | 5/1980 | Ellson . |
| 4,896,547 | 1/1990 | Arney et al. . |
| 4,964,309 | 10/1990 | Jenkins . |
| 4,987,767 | 1/1991 | Corrigan et al. . |
| 5,200,614 | 4/1993 | Jenkins . |
| 5,491,337 | 2/1996 | Jenkins et al. . |
| 5,585,575 | 12/1996 | Corrigan et al. . |
| 5,753,832 | 5/1998 | Bromberg et al. . |

*Primary Examiner*—Robert Raevis
*Attorney, Agent, or Firm*—Anthony J. Casella; Gerald E. Hespos; Michael J. Porco

[57] ABSTRACT

A portal is provided for use with a detector for detecting trace amounts of contraband that may be retained on skin or clothing of the human subject. The portal relies upon the continuous process by which microscopic flakes of skin continuously separate from human subjects. The portal further relies upon the existence of a human thermal plume consisting of a layer of warm air adjacent the all human subject. The warm air rises in the cooler surrounding air and transports the microscopic flakes of skin upwardly. The portal capitalizes on this phenomenon by providing at least a partial enclosure with a funnel-shaped collector above the human subject. A low speed flow of relatively dense cool air may be introduced into the portal to buoyantly lift the warmer air of the human thermal plume upwardly. The air stream defined by the human thermal plume and the skin particles therein moves to a trap in the funnel-shaped collector above the portal. The trap cooperates with a detector for detecting the presence of molecules of interest.

18 Claims, 3 Drawing Sheets

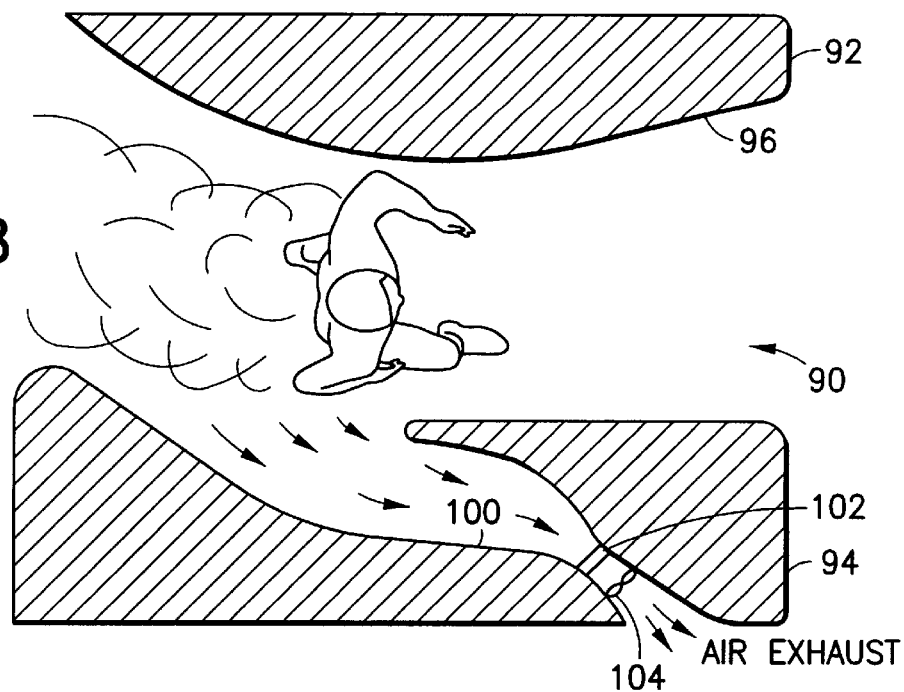
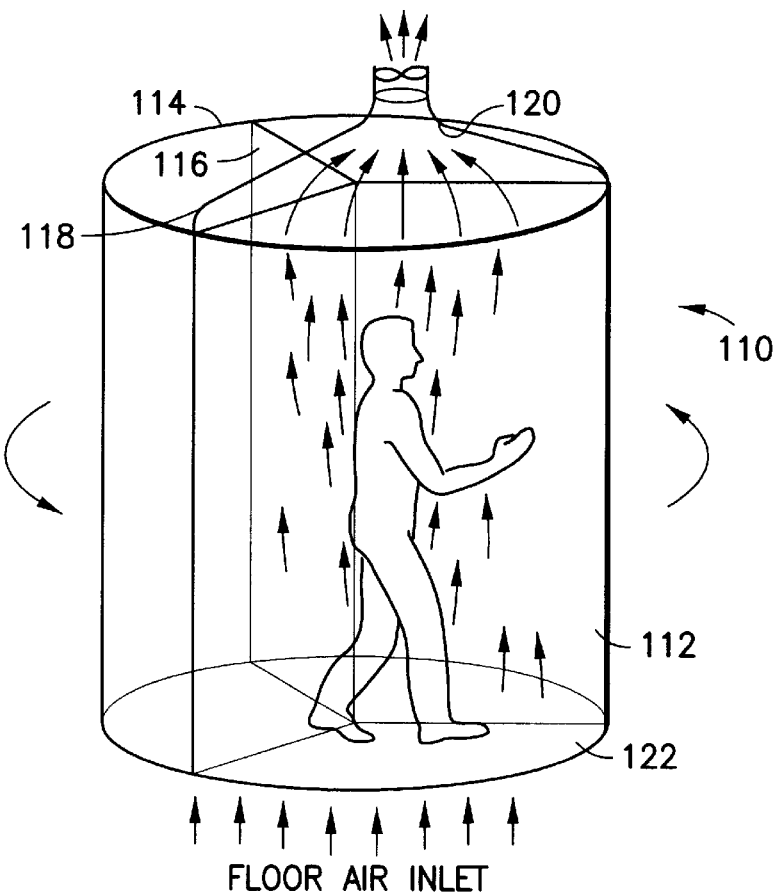

CHEMICAL TRACE DETECTION PORTAL BASED ON THE NATURAL AIRFLOW AND HEAT TRANSFER OF THE HUMAN BODY

This Application claims benefit of Provisional application 60/077,736 Mar. 12, 1998.

BACKGROUND OF THE INVENTION

1. Field of the Invention

The present invention relates to a portal-type sampling system for sampling the air around human beings for purposes of detecting trace chemicals present therein.

2. Description of the Related Art

The rise in worldwide terrorism, especially directed at commercial air transportation, has made it imperative that airport passenger security stations screen for concealed explosives as well as for metallic weapons. Experience has shown that concealed explosive devices have been carried onboard aircraft by terrorists on a number of occasions, some of which have resulted in disasters claiming the lives of all persons onboard. Further, the modern terrorist is sophisticated enough to obtain and use plastic explosives, a small amount of which may be sufficient to bring down an aircraft, and which are very difficult to detect.

It is well-known that specially-trained dogs can detect such concealed explosives under the proper circumstances, despite the fact that the concentration of explosive in the air may be as little as a few parts per trillion. Chemical detection devices of exquisite sensitivity have also been developed, based on the principles, for example, of mass spectrometry, ion-mobility spectrometry, or gas chromatography. Very effective devices are shown, for example, in U.S. Pat. No. 5,200,614 which issued to Anthony Jenkins and in U.S. Pat. No. 5,491,337 which issued to Anthony Jenkins and William J. McGann. Commercialized detectors that incorporate the technology of U.S. Pat. No. 5,200,614 and U.S. Pat. No. 5,491,337 typically function by initially rubbing a wipe over an article, such as a piece of luggage, that is likely to carry a trace amount of a composition of interest. The wipe then is placed in an apparatus employing the technology of U.S. Pat. No. 5,200,614 or U.S. Pat. No. 5,491,337, and an air stream is directed through the wipe to transport trace amounts of molecules of interest into the apparatus for detection. A wipe cannot realistically be rubbed across the body of a passenger to test for compositions of interest. Therefore, what has been lacking in the prior art is a rapid, convenient, socially-acceptable means for such sensors to sample the intimate environment of human subjects to screen for concealed explosives.

A hand-held sensor attached to one of the detection devices mentioned above has been used in the prior art to carry out a body-scan of an individual. Such a device is marketed by Ion Track Instruments, Inc. of Wilmington, Mass. under the trademark "VAPOR TRACER". This type of device can be used effectively at vehicle border crossings for detecting the presence of certain explosives or narcotics. However, this prior art device would be very time-consuming when applied to the many thousands of airline passengers who travel each day, and would be perceived as an intrusive approach which would be likely to elicit objections if used on a significant proportion of those passengers boarding an airplane.

Less intrusive means of screening passengers for concealed explosives have been proposed. One such prior art device is disclosed in U.S. Pat. No. 4,045,997 which issued to Showalter.

The Showalter patent discloses a horizontal "air curtain" passing between two cabinets, through which curtain human subjects pass. The air curtain is intended to "strip off" trace vapors of concealed explosive. The vapors were intended to be detected by certain sensors mounted in the receiving cabinet of the air curtain.

U.S. Pat. No. 4,202,200 issued to Ellson discloses a 10-foot-long, 7-foot-high, 3-foot-wide corridor including means to produce a horizontal circulation of air leading to a recirculation zone in the center of the device. Subjects walking through this portal are impinged upon by the recirculating airstream. As a result, it is intended by Ellson that "explosive vapor is stripped from the person by the airstream." It was further asserted by Ellson that the circulatory nature of the airflow does not further dilute the explosive vapor.

U.S. Pat. No. 4,896,547 issued to Achter et al. and discloses a "walk-in, walk-out" booth containing suction vents which horizontally draw in a "large volume" of air from around a human subject who enters the booth. Further, arrays of air-jet "puffers" and infrared strip heaters in the booth serve to "dislodge (explosive) vapors, expel air from beneath clothing, scrub vapors from exposed skin, and disrupt stagnant boundary layers of air near the person." The Ellson patent is intended to collect a non-representative sample (e.g. of less than the entire human body). A key of the Achter et al. patent is that it samples from "essentially the entire body." This patent also defines "vapor" to mean any of gas-phase, aerosol, or small-solid-particle explosive residues. The Ellson patent also asserts that a traditional metal detector may be integrated into the explosive-detection booth.

U.S. Pat. No. 4,964,309 issued to Jenkins et al. and reviewed some of the above prior art and concluded that explosive detectors of the air-curtain-type dilute explosive vapors with excess air and reduce their concentrations by as much as 100,000-fold. The Jenkins et al. patent further noted that problem with the prior art cannot be solved simply by reducing the airflow rates of such devices, since this measure would reduce the "leaching" effect of airflow on the human subject, increase losses due to natural room-air currents, and increase the sampling time unacceptably. The Jenkins et al. patent therefore proposed a different type of portal in which subjects must pass through swinging "saloon-doors" which make physical contact with the body, and which are fitted with suction pipes to remove a small sample of air from the intimate vicinity of the body. It was asserted that the physical contact of subjects with these doors removes explosive vapors from clothing and samples said vapors while not diluting them with excess volumes of air. A sampling flow rate of 0.05 to 0.2 liters/sec (0.1 to 0.4 cfm) of air was enabled due to the direct physical contact, as compared to 200 liters/sec (400 cfm) or more in air-curtain-type prior art.

U.S. Pat. No. 4,987,767 and U.S. Pat. No. 5,585,575 issued to Corrigan et al. and returned to the concept of a walk-through portal involving no physical contact with subjects, but rather an array of airjets in a recirculating air-curtain-type setup. The configuration of these airjets is claimed to "effectively isolate the internal air volume from the ambient environment." Airjets from the periphery of the portal are aimed toward the center, through which the human subject walks. The airstream is collected at the ceiling of the portal and recirculated to the airjets, after a "small amount" is drawn off for purposes of explosive vapor detection. As in the prior art, a 6-foot-long, 7-foot-high, 3-foot-wide corridor is provided for the passage of persons being screened, each person spending 2–3 seconds inside the portal. Some 2400 liters/sec (4800 cfm) of air are recirculated in total, passing through an array of airjets which produce exit airspeeds of 17 m/sec. It is specifically claimed in this patent that the directions of these airjets are critical to the functioning of the portal.

The above-described prior art perceived a need to strip, scrub, or otherwise dislodge explosive vapors and/or particles from the skin and clothing of human subjects. These vapors and/or particles are presumed to be stagnant and to require active disruption and removal in order to provide a sufficient signal to an explosives-detection analyzer.

The "sampling" action of the prior art, i.e. removing the explosive signal from the human subject and presenting it to an appropriate detector, is accomplished by a variety of intrusive means including strong air currents, continuous or intermittent impinging air jets, infrared heaters, and physical contact by swinging doors or similar devices.

Air currents used in the above-described prior art for purposes of dislodging particles from human subjects are generally oriented horizontally with respect to the vertical orientation of a standing human subject. Only in the Corrigan et al. patent is the air-current orientation not entirely horizontal (a few of the airjets in this case are oriented upward at a 45-degree angle to the horizontal).

The above-described prior art that avoids physical contact relies instead upon the movement of very large quantities of air compared to the thin layer of air surrounding the human body (to be discussed below). For those examples of the prior art that avoid physical contact, the minimum airflow is about 200 liters/sec (400 cfm) in the case of the Showalter patent, while the maximum airflow is 2400 liters/sec (4800 cfm) in the case of the Corrigan patent. This leads to a very great dilution of the chemical traces released by a subject with concealed explosives. Given such dilution, the task of detecting a vanishingly low concentration of explosive or other chemical trace in a large mass of air becomes essentially an impossible one.

The above-described prior art devices generally sample only a small portion of the airstream they create. Since available explosive analyzers can accept only a very small sample size, typically much less than 1 liter/sec, most of the generated airflow is not examined at all for the presence of trace explosives. Solid particulates are not specifically sampled or, if they are, they are subsequently boiled off to present a gaseous sample to the chemical analyzer. This heating must be done carefully to avoid decomposing the very compounds one is looking for. In the case of the Corrigan patent, a "small amount" of the recirculated airstream is drawn off for purposes of explosive vapor detection and a multi-step concentration scheme then is used in an attempt to present a higher concentration of possible trace explosives to a chemical analyzer than would otherwise be available.

The prior art recognizes that some combination of explosive vapor and/or particulates is or may be involved in the proper functioning of an explosive-detection portal. It is further asserted that such portals have broader applications, i.e. in drug and hazardous-materials detection as well. Finally, it is noted that the functions of explosive detection and metal detection, as for concealed weapons, may be integrated into a single portal-type device.

SUMMARY OF THE INVENTION

The subject invention is based partly on the premise that the art of explosive-detection portals for human subjects may be substantially improved by taking proper account of the thermal behavior of the air surrounding the human body, and of the natural particulate field generated by the continuous shedding of the outer human skin layer. As will be shown below, such consideration is central and crucial to the effective detection of concealed explosives or other substances on the human body. Further, active stripping, scrubbing, or other removal of trace explosives from the body and clothing by mechanical means or air-jet impingement is either unnecessary, insofar as this function is automatically performed by the natural behavior of the human thermal plume itself, or only becomes necessary under such circumstances that the natural signal produced by the body is too weak to detect. The concept of a "stagnant boundary layer" of explosive vapor on or near the human body, as described in the prior art, is actually not physically possible within the context of the known behavior of the human thermal plume. In contrast with the horizontal orientation of air currents in the preponderance of the prior art, the subject invention takes advantage of the natural orientation of the thermal plume of a standing human, which, as discussed below, is vertical and upward. The prior art thus introduces airflow patterns at direct variance with the natural tendency of the convective airflow about the body, leading to gross inefficiencies in the collection of a concentrated sample of air from the intimate environment of the human body.

The 4800 cfm recirculation produced in the case of the Corrigan patent, for example, is some 50–80 times the airflow produced by the entire human thermal plume (30–50 liters/sec or 60–100 cfm).

The present invention is based on the inherent thermal and aerodynamic characteristics of the human body, and secondarily on the presence of a large number of human skin flakes in the air surrounding the body. The human skin is normally several degrees warmer than the surrounding atmosphere (averaging 33 C skin temperature vs. 24 C room temperature). This causes continuous thermal convection to occur from the body to the surrounding atmosphere. With normal activity levels, the rate of energy transferred by the body to the air is about 80 Watts. It is by this mechanism that waste heat is rejected by the body and thermoregulation of the body occurs. (Further details on these topics may be found in *Man and His Thermal Environment*, by R. P. Clark and O. G. Edholm, E. Arnold Publishers, London, 1985, and Settles, G. S., Gowadia, H. A., S. B. Strine, T. E. Johnson, "The Natural Aerodynamic Sampling of Trace Explosives from the Human Body," Proc. of the $2^{nd}$ FAA Symposium on Explosives Detection Technology and Aviation Security Technology Conference, 12–15 November 1996, Atlantic City, N.J., ed. W. H. Makky, pp. 65–70).

The air heated by the skin, being warmer and less dense than the surrounding air, rises naturally according to Archimedes' Principle. This generates a human boundary layer. For a standing person, the boundary layer begins at the ankles and travels up the legs and torso, growing thicker and faster as it moves. Around the upper body, the human boundary layer is several cm thick and has a vertically-upwardly-directed speed of as much as 0.5 m/sec. At the shoulders and head this boundary layer leaves the body and continues its buoyant upward motion, forming the human thermal plume. The airflow contained in the entire plume is on the order of 30–50 liters/sec or 60–100 cfm. The human boundary layer and plume are observed to form in about the same manner despite wide variations in body height, weight, amount or style of clothing, etc.

It is thus essential to the present invention that the air in contact with the body is never stagnant, but is in a constant state of upward motion. Moreover, the very nature of the motion of the human boundary layer is such that every location on the surface of the body contributes to it. Thus any location where explosives might be concealed, such as the ankles, legs, thighs, waist, arms, etc., all contribute about equally (per unit skin area) to the buoyant airstream which eventually rises above the body to form the thermal plume. Traces of explosives concealed anywhere on the body thus migrate naturally upwardly and end up in the thermal plume. The clothing does not significantly interfere with this process, except when it traps some of the trace particulates, or in the unlikely case of its being impermeable and hermetically sealed at wrists, ankles, neck, and waist.

The subject invention operates on the principle that sampling must encompass the entire human body in order to insure that concealed explosives are not overlooked. The human thermal boundary layer accomplishes this task naturally, so that one need only collect the thermal plume rising naturally above the head of a subject to have a highly-concentrated sample from all locations on the body. Moreover, insofar as this task is accomplished naturally by the human thermal plume, it is highly undesirable to dilute and/or diffuse the plume by artificially-induced air currents, as is done in essentially all prior art in this field.

The subject invention also takes advantage of certain facts that are well-known in the non-analogous medical and physiological arts, namely, that human beings shed their outer skin layer continuously in the form of microscopic flakes or scales (see, e.g., *Physiology and Biochemistry of the Skin*, S. Rothman, Chicago, 1954). It has been found that the entire outer layer of skin is shed every one or two days. For an average body surface area of 1.8 square meters and an average skin-flake diameter of 14 microns, it turns out that some millions of skin flakes are shed by the average person every minute. Indeed, tests of indoor environmental dust in homes and offices have shown it to be primarily composed of human skin.

The skin flakes released by the epidermis are immediately caught up in the upward motion of the human boundary layer, since their settling speed is only 1 mm/sec to, at most, 1 cm/sec. Further, since their average size is much smaller than the interweave pores of almost all clothing fabrics, they move freely through the clothing and away from the site where they were released. (This is proved by the fact that counts of bacteria shed from the body on skin flakes are about the same whether subjects are clothed or nude.) So it is that the thermal plume of a typical person, while walking, conveys some 7 million skin flakes away from the body each minute. The entire human boundary layer is thus a heavily particle-laden flow containing an extremely large number of microscopic skin flakes. All regions of the body generate such flakes, and the thermal plume of the body likewise contains myriad skin flakes that have originated from all regions of the body. A rough estimate of the total mass of skin flakes transported by the human thermal plume is ⅓ milligram/second. It thus seems likely that the sheer numbers and ubiquitous nature of these skin flakes insures that they provide a very large "cross-section" upon which trace explosives can be adsorbed. Those explosive molecules already released by concealed explosives and adsorbed on nearby skin will likewise be transported by skin flakes due to the continuous shedding of the latter.

Accordingly it is highly desirable to collect the approximately 30–50 liters/sec of rising warm air in the human thermal plume and extract the approximately ⅓ milligram/sec of solid skin flakes it contains, along with textile fibers from the clothing which may also have adsorbed traces upon them, thereby rejecting the air and retaining only the small solid sample with adsorbed trace explosives. This highly-concentrated sample is then presented directly to an appropriate device for analysis and detection. Due to the high nitrogen content of explosives, the technology already exists to distinguish them from other components of the sample, presuming that a sufficient concentration of trace explosives is present. (See, for example, "Explosive Detection for Aviation Security" by A. Fainberg, *Science*, Vol. 255, Mar. 20 1992, pp. 1531–1537, and "Vapor Detection of Explosives" by D. H. Fine and E. K. Achter, in ASTM STP 1127, 1992, pp. 45–49.) Furthermore, concealed narcotics and other hazardous materials or controlled substances may be detected in the same manner, and a human mitochondrial DNA sample may be extracted from the captured skin-flake sample.

It is important to establish that although the following detailed description is framed in terms of the detection of concealed explosives, this invention has broader and more general applications as well. Specifically, the principles disclosed here may similarly be used to detect other illegal and/or dangerous substances concealed upon or inside the human body, such as contraband drugs, incendiaries, money, and chemical/biological warfare agents. Further, it is possible with the portal invention disclosed here to collect a small sample of human skin flakes shed by subjects passing therethrough, from which a human DNA sample can be extracted for purposes of DNA typing of individuals. One embodiment of the presently-disclosed invention may be used to detect trace biological signals emitted by the human body, which signals can be keyed to the subject's state of health, thereby allowing any of a wide variety of diseases to be diagnosed without direct physical contact. Finally, the present invention may be used to detect traces of controlled nuclear substances, such as Uranium, which are difficult to detect by traditional radiation detectors.

The collection of the human thermal plume without dilution by extraneous air is accomplished by an open, walk-through portal with an overhead collector, beneath which human subjects are required to pause for a few seconds. This collector may have an inverted, contoured funnel shape, terminating in a filter, trap, or particulate separator and a single fan or blower which draws the air of the plume through the collector. The filter, trap, or separator may be any one of several different devices including 1) a mesh filter-type separator, 2) a cyclone-type separator, 3) an impingement/particle-inertia-type separator, 4) an electrostatic precipitator, 5) a cold trap, or some other device known to the prior art and not specifically covered in this disclosure. Likewise the explosives, narcotics or other chemical detector to which the resulting sample is presented may be a prior art detector, such as the detectors disclosed in U.S. Pat. No. 5,200,614 or U.S. Pat. No. 5,491,337, the disclosures of which are incorporated herein by reference.

BRIEF DESCRIPTION OF THE DRAWINGS

FIG. 8 is a top plan view of a portal to collect a sample from the human thermal wake.

FIG. 9 is a perspective view of a revolving-door type of positive displacement sampling portal.

DETAILED DESCRIPTION OF THE PREFERRED EMBODIMENTS

Figure 1:
FIG. 1 is a sketch of a human thermal boundary layer and plume.

The portals of the subject invention capitalize on physical and physiological phenomena identified by the inventor herein and illustrated schematically in FIG. 1. In particular, FIG. 1 depicts a human subject S standing on a substantially horizontal floor F. The human subject S typically will have a body temperature that exceeds the temperature of the ambient air adjacent to the human subject S. The body heat of the human subject S will cause a warming of air adjacent to the human subject S. This warmed air will effectively define a boundary layer of warm air in close proximity to the human subject S. Warm air is less dense than cooler air. As a result, warm air rises relative to cooler air. This known physical phenomenon causes the warm air boundary layer adjacent the human subject S to gradually flow upwardly and through the cooler air at further distances from the human subject S. This upwardly flowing air is identified by arrows "A" in FIG. 1 and collectively defines a human thermal plume.

The human thermal plume cooperates with another physiological phenomena referred to above. In particular, the human subject H continually emits microscopic particles of dead skin as part of the skin regeneration process described above. These microscopic particles of dead skin are entrained in the upwardly flowing air A that forms the human thermal plume illustrated schematically in FIG. 1.

Figure 2:
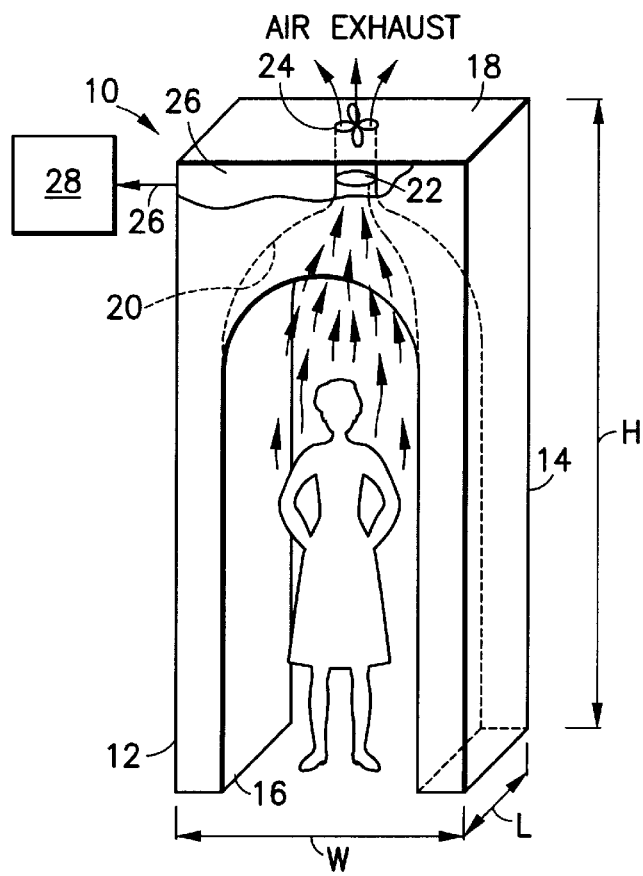
FIG. 2 is a perspective view of a portal in accordance with the subject invention.

A walk-through screening portal for purposes of detection of concealed explosives, narcotics, and other sensitive or dangerous substances, or for the possible collection of human DNA samples, or for the sampling of airborne signals related to the state of health of human subjects, is identified generally by the numeral 10 in FIG. 2. The portal 10 has two substantially vertical sidewalls 12 and 14 that are spaced sufficiently from one another to form an open passage 16 through which a human subject may conveniently pass. Preferably, the sidewalls are spaced from one another to define an overall width "W" of approximately 3 feet. Additionally, the sidewalls 12 and 14 define an overall length "L" of approximately three feet. The portal 10 further has a ceiling 18. The ceiling is disposed above the floor or supporting surface for the portal 10 by a distance sufficient to define an overall portal height "H" of between approximately 7–10 feet. These dimensions enable most human subjects to pass easily through passage 16 of the portal 10.

The sidewalls 12 and 14 and/or the ceiling 18 may further be provided with a metal detector comparable to commercially available metal detectors commonly employed at airports and other locations requiring security. Thus, the contraband detection functions of the portal 10, as explained herein, may be carried out simultaneously with the metal detection functions in an apparatus that is dimensionally comparable to the currently employed metal detectors.

Portions of the ceiling 18 that cover the open passage 16 define an inverted contoured funnel 20 that gradually tapers to smaller cross-sectional dimensions at locations further above the passage 16. The funnel 20 is operative to collect the rising thermal plume generated by the human body as explained above. The smaller cross-sectional portions of the funnel 20 are provided with a filter, trap or separator identified generally by the numeral 22 in FIG. 2. For ease of reference, the filter, trap or separator 22 will be referred to herein simply by the generic term trap. However, this generic term is not intended to be structurally or functionally limiting. Rather, the trap 22 is any known structure with the ability to extract from the human thermal plume a sample of particulates, such as skin flakes with adsorbed compounds thereon or airborne trace chemical in vapor form. Comparable traps are used in commercially available contraband detectors marketed by Ion Track Instruments, Inc.

A fan 24 or other air circulation generator is provided to generate an air flow that will direct the human thermal plume through the trap 22.

The air drawn through the fan 24 then is expelled to the environment. A conveyor 26 is further provided to present the trap 22 to a substance detector 28 which is schematically illustrated in FIG. 2. As noted above, the substance detector 28 may be a prior art detector, such as one of the highly effective detectors shown in U.S. Pat. No. 5,200,614 or U.S. Pat. No. 5,491,337.

Figure 3:
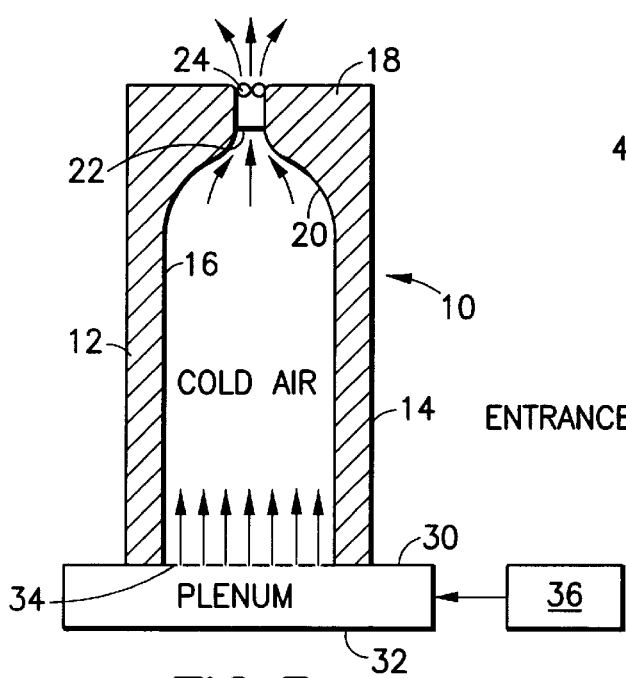
FIG. 3 is a cross-sectional view of the portal shown in FIG. 2, also including a cold air plenum at its floor.

The portal 10 described above and illustrated in FIG. 2 may be positioned on a floor 30 having a plenum 32 formed therein. The plenum 32 may communicate with the open passage 16 through a plurality of small air apertures 34. The plenum 32 also may communicate with an air flow generator which is illustrated schematically in FIG. 3 and identified generally by the numeral 36. The air flow generator 36 may be operative to direct cold air uniformly through the plenum 32, upwardly through the apertures 34 and into the open passage 16 at a speed of no more than approximately 0.5 meter/sec. The flow of cold air at a low speed of no more than 0.5 meter/sec. will not function to effectively scrub the human subject and will not add significantly to the volume of air presented to the funnel 20. Rather, the cold air directed through the plenum 32 merely will enhance and speed the natural vertical motion of the warm human thermal plume "A" due to buoyancy effects of the warm boundary layer of air containing the human thermal plume riding above the colder air directed into the passage 16 through the plenum 32. The temperature of the air directed through the plenum preferably should be several degrees cooler than ambient, but need not be so cold as to cause discomfort to the human subject in the portal 10. An air temperature through the plenum 32 of approximately 60° F. will be sufficient to provide the desired buoyancy effect.

Figure 4:
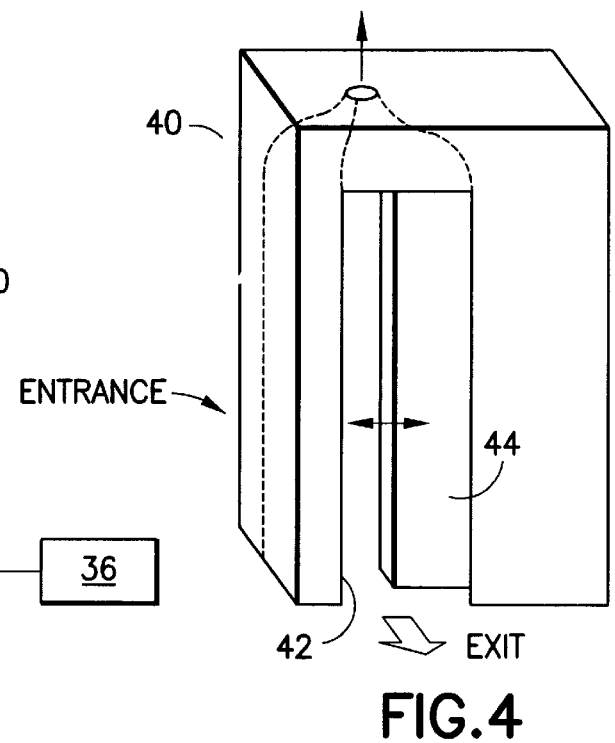
FIG. 4 is a perspective view of a portal with a clear sliding exit door.

An alternate portal is identified generally by the numeral 40 in FIG. 4 and is structurally and functionally similar to the portal 10 described above and illustrated in FIG. 2. The portal 40, however, is provided with a passage 42 having a clear plastic sliding door 44 at the exit from the passage 42. The door 44 inhibits a through flow of extraneous air that may be attributable to room air currents. Additionally, the door 44 provides a more efficient and accurate sequencing of the passage of human subjects through the portal 40, and thereby ensures a more accurate matching of detection data with human subjects.

Figure 5:
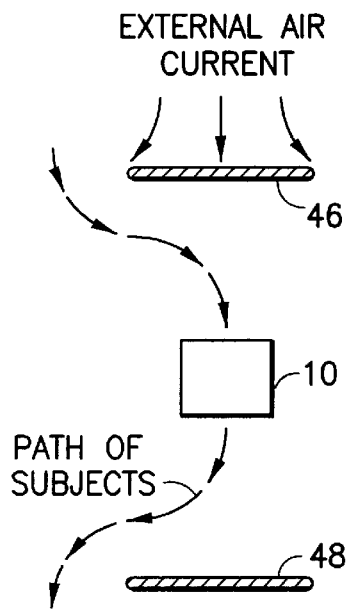
FIG. 5 is a top plan view of a portal with two separate baffle panels for the suppression of external air currants.

The impact of external air currents can be minimized without the provision of a mechanical sliding door as part of the portal. In this regard, FIG. 5 shows the portal 10 of FIG. 2 used in combination with upstream and downstream baffles 46 and 48. The baffles effectively block a through flow of extraneous air due to room air currents and further contribute to proper sequencing of human subjects through the portal 10 and effective matching of detection data to the respective human subjects. The baffles 46 and 48 preferably are spaced between 3 and 6 feet from the portal 10.

Figure 6:
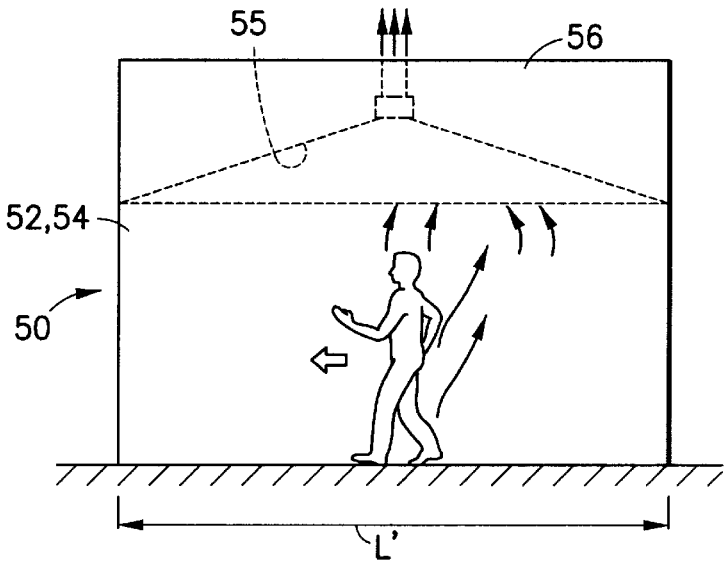
FIG. 6 is an elongated walk-through portal with a ceiling collector.

The portal of the subject invention need not be dimensionally comparable to a commercially available metal detector. Rather, FIG. 6 shows an elongated corridor-type of portal that is identified generally by the numeral 50. The corridor portal 50 preferably has a width of approximately 3 feet and a height in the range of 7–10 feet, both of which are comparable to the width and height dimensions of the above-described portal 10. However, the portal 50 illustrated in, FIG. 6 preferably has a length L' of approximately 6–10 feet. Thus, the portal 50 is at least 2–3 times greater in length than the portal 10 described above. The portal 50 may further be provided with sidewalls 52 and 54 formed from a clear plastic material. The clear plastic sidewalls eliminate the claustrophobic effect of the portal 50. As in the previous embodiments, the portal 50 is provided with a ceiling 56 having an inverted funnel collector 58 formed on interior surfaces thereof. However, the funnel 58 of the portal 50 is more elongated.

The clear plastic walls 52 and 54 further enable observation of human subjects by security personnel working near the portal 50. This ability to observe human subjects can lead to visual observation of erratic behavior that may justify more detailed searching.

Figure 7:
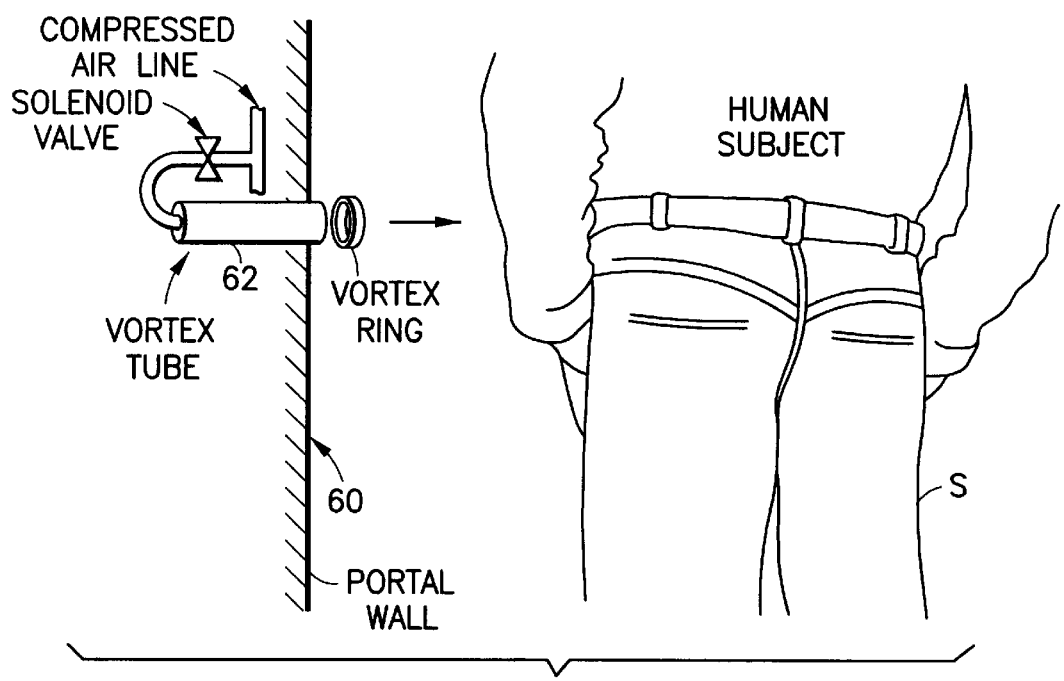
FIG. 7 is a cross-sectional view of a portal employing a vortex-ring impinger.

FIG. 7 is a cross-sectional view of a portal 60 that is structurally and functionally similar or identical to the portals 10, 40 or 50 as described and illustrated above. However, the portal 60 is provided with a vortex-ring generator 62 designed and located to impinge a level of airborne kinetic energy on the clothing of human subjects passing therethrough for purposes of agitating said clothing to remove trace solids of substances adsorbed thereto. However, the vortex-ring generator 62 provides primarily only a local airflow disturbance and does not significantly alter the natural airflow rate of 30–50 liters per second in the human thermal plume, and does not alter the naturally upward direction of flow of the human thermal plume as illustrated schematically in FIG. 1 above.

FIG. 8 shows another embodiment of a portal which is identified generally by the numeral 90. The portal 90 includes first and second spaced apart sidewalls 92 and 94 forming a passage 96 therethrough. A ceiling extends across the top of the sidewalls 92 and 94. The portal 90 differs from those described above in that it has no funnel-shaped collector in the ceiling. Rather, a funnel-shaped airflow collector 100 is provided on the sidewall 94. The funnel collector 100 is disposed and configured to take advantage of a thermal wake being formed behind a human subject passing through the portal 100. A trap 102 is provided in the narrow portion of the funnel 100 and functions to extract from the human thermal wake either particulates, such as skin flakes with adsorbed compounds thereon, or airborne trace chemicals in vapor form. Thus, the trap 102 is structurally and functionally similar to the trap 22 described with respect to the embodiment of FIG. 2. A blower 104 is provided in proximity to the trap 102 and generates a low speed airflow to draw the human thermal wake through the trap 102 and to expel the remaining airstream to the environment. As in the previous embodiment, the conveyance means is provided to present the trapped sample to a substance detector for each human subject passing through the portal 90. As in the previous embodiments, the detector is operative to detect the presence of molecules of interest.

FIG. 9 shows an embodiment of the invention that is structurally and functionally similar to the embodiment of FIG. 4. More particularly, FIG. 9 shows a portal 110 having sidewalls 112 and 114 each of which is substantially cylindrically generated about a common axis and with identical radii. The walls 112 and 114 are separated from one another to define an entrance to the portal 110 and an exit therefrom. A revolving door 116 is rotatably disposed centrally between the walls 112 and 114. The portal 110 further includes a ceiling 118 having a funnel shaped collector 120. However, the funnel 120 is configured to overlie only a portion of the ceiling extending between the entry and exit ends of the sidewall 112. Thus, the funnel 118 does not continuously draw from the ambient environment and is at least partly isolated from portions of the portal 110 adjacent the sidewall 114. The portal 110 further includes a plenum 122 that is configured and disposed to substantially register with the funnel 120. However, the plenum 122 is disposed in the floor at the bottom end of the portal 110. The plenum 122 functions substantially as the plenum in the embodiment of FIG. 3 by generating a low flow of cool air that encourages the human thermal plume to float upwardly due to the buoyancy effects of the less dense warm air defining the human thermal plume. The portal 110 shown in FIG. 9 includes all other structural and functional components of the other embodiments, including a trap, conveyor means for delivering the trap to a detector and a detector that functions to identify certain molecules of interest.

While the invention has been described with respect to a preferred embodiment, it is apparent that various changes can be made without departing from the scope of the invention as defined by the appended claims.

What is claimed is:

1. A portal for collecting substances of interest from a human subject passing therethrough, said portal comprising a plurality of sidewalls spaced from one another sufficiently to define a passage extending therebetween, said sidewalls defining an entry to said passage and an exit therefrom, said entry, said exit and said passage being dimensioned for accommodating passage of the human subject through said portal, a ceiling extending across and connecting top portions of said sidewalls and covering said passage, portions of said ceiling adjacent said passage defining a collector, said collector comprising fan means for collecting air heated by body heat of the human subject and rising upwardly adjacent the human subject as a human thermal plume of heated air at a flow rate on the order of approximately 30–50 liter/sec, said fan means being operative for accommodating the air in the human thermal plume without substantial dilution of air in the human thermal plume by extraneous air.

2. The portal of claim 1, further comprising a trap removably positioned in the collector, said trap being selected from a material for permitting passage of air therethrough but for trapping particulates and substances of interest in said air.

3. The portal of claim 2, further comprising means for periodically transferring said trap to a detector.

4. The portal of claim 1, further comprising at least one baffle spaced externally of said passage a sufficient distance to enable a human subject to enter and leave said passage of said portal at said entry and exit therefrom, said baffle being dimensioned to substantially block external air currents from entering said portal.

5. The portal of claim 1, further comprising a selectively openable door for impeding flow of external air currents through said portal.

6. The portal of claim 1, wherein at least one of said sidewalls is formed from a transparent material.

7. The portal of claim 1, wherein said sidewalls are spaced from one another by a selected distance, each said sidewall defining a length measured substantially parallel to said ceiling that is substantially greater than said distance between said sidewalls.

8. The portal of claim 1, wherein portions of said ceiling adjacent said passage define a funnel-shape with a large cross-section adjacent said passage and a smaller cross-section at locations on said collector further from said passage.

9. A method for collecting from a human subject trace amounts of contraband, said method comprising the steps of:

providing a portal with at least a pair of spaced apart side walls extending upwardly from a floor and a ceiling extending across portions of said sidewalls remote from said floor, said sidewalls and said ceiling defining a passage therebetween, said passage being dimensioned for enabling the human subject to walk therethrough;

placing a trap in proximity to said ceiling and in communication with said passage, said trap being formed from a material for trapping particles of skin released from said human subject;

directing said human subject through said passage such that a human thermal plume of heated air produced by body heat of said human subject exists in said passage, said air in said human thermal plume rising in proximity to said human subject in said passage at a plume flow rate on the order of approximately 30–50 liter/sec;

generating a flow of air through said trap for accommodating air in said human thermal plume substantially at said plume flow rate and without diluting the air in said human thermal plume by artificially-induced air currents from outside said portal;

directing said human subject out of said passage; and conveying said trap to a contraband detector after passage of said human subject through said passage.

10. The method of claim 9, further comprising directing a flow of cool air through said floor at said passage for buoyantly lifting warmer air upwardly and toward said trap.

11. The method of claim 10, wherein said step of directing cool air through said floor of said passage comprises directing said air at a speed of no more than approximately 0.5 meter/sec.

12. The method of claim 11, comprising the step of cooling said air to approximately 60° F.

13. A portal for collecting substances of interest from a human subject passing therethrough, said portal comprising a plurality of sidewalls spaced from one another sufficiently to define a passage extending therebetween, said sidewalls defining an entry to said passage and an exit therefrom, said entry, said exit and said passage being dimensioned for accommodating passage of the human subject through said portal, a ceiling extending across and connecting top portions of said sidewalls and covering said passage, a collector being formed in said ceiling for collecting skin flakes separated from said human subject walking through said passage of said portal, a trap being movably positioned in said collector, a blower in communication with the collector for generating a flow of air at a speed of no more than approximately 0.5 meter/sec from said passage through said trap and at a flow rate sufficient to accommodate a human thermal plume produced by heat of the human subject and rising from the human subject at a flow rate on an order of approximately 30–50 liters/sec such that said blower does not significantly dilute said human thermal plume by artificially induced air currents and extraneous air, and a conveyor for selectively moving said trap from said collector for analysis.

14. A portal for collecting substances of interest from a human subject passing therethrough, said portal comprising a plurality of sidewalls spaced from one another sufficiently to define a passage extending therebetween, said sidewalls defining an entry to said passage and an exit therefrom, said entry, said exit and said passage being dimensioned for accommodating passage of the human subject through said portal, a ceiling extending across and connecting top portions of said sidewalls and covering said passage, portions of said ceiling adjacent said passage defining a collector, said collector comprising means for collecting airflow generated by body heat of the human subject without substantial dilution by extraneous air, a plenum disposed beneath said passage, a perforated floor between said plenum and said passage for permitting a flow of air from said plenum into said passage, said plenum further being in communication with a supply of cool air at a temperature cooler than ambient air, a blower for directing said cool air from said plenum into said passage, said cool air from said plenum buoyantly enabling warm air adjacent said human subject to rise toward said collector.

15. The portal of claim 14, wherein said blower is operative to direct said cool air at a speed of no more than approximately 0.5 meter/sec.

16. The portal of claim 15, wherein the cool air has a temperature of about 60° F.

17. A portal for collecting substances of interest from a human subject passing therethrough, said portal comprising a plurality of sidewalls spaced from one another sufficiently to define a passage extending therebetween, said sidewalls defining an entry to said passage and an exit therefrom, said entry, said exit and said passage being dimensioned for accommodating passage of the human subject through said portal, a ceiling extending across and connecting top portions of said sidewalls and covering said passage, portions of said ceiling adjacent said passage defining a collector, said collector comprising means for collecting airflow generated by body heat of the human subject without substantial dilution by extraneous air, wherein the sidewalls of the portal are substantially cylindrically generated about a common axis, said door being a revolving door disposed between said sidewalls, the collector being between the central axis of said sidewalls and one of said sidewalls.

18. A portal for collecting substances of interest from a human subject passing therethrough, said portal comprising a plurality of sidewalls spaced from one another sufficiently to define a passage extending therebetween, said sidewalls defining an entry to said passage and an exit therefrom, said entry, said exit and said passage being dimensioned for accommodating passage of the human subject through said portal, a ceiling extending across and connecting top portions of said sidewalls and covering said passage, portions of said ceiling adjacent said passage defining a collector, said collector comprising means for collecting airflow generated by body heat of the human subject without substantial dilution by extraneous air, at least one vortex tube mounted to at least one said wall of said portal, said vortex tube having a first end communicating with said passage through said portal and a second end spaced from said passage, a supply of compressed air communicating with said second end of said vortex tube for selectively producing a vortex ring for delivering airborne kinetic energy to the human subject passing through said portal sufficient to agitate clothing of said human subject and remove trace solids of substances adsorbed thereto without significantly altering the natural airflow adjacent said human subject.

* * * * *